US00PP34269P2

(12) United States Plant Patent
Hansen

(10) Patent No.: US PP34,269 P2
(45) Date of Patent: May 24, 2022

(54) ***HOSTA* PLANT NAMED 'WILD IMAGINATION'**

(50) Latin Name: ***Hosta* hybrid (Tratt.)**
Varietal Denomination: Wild Imagination

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 17/300,991

(22) Filed: Jan. 13, 2022

(51) Int. Cl.
*A01H 5/02* (2018.01)
*A01H 6/12* (2018.01)

(52) U.S. Cl.
USPC ..... Plt./353
CPC ..... *A01H 6/12* (2018.05)

(58) Field of Classification Search
USPC ..... Plt./353
CPC ..... A01H 5/02; A01H 5/12
See application file for complete search history.

*Primary Examiner* — Kent L Bell

(57) ABSTRACT

A new and distinct *Hosta* plant named 'Wild Imagination' with medium-sized, rounded-mound habit of glaucous, bluish-green, long thin foliage. Leaves have are twisted distally and very wavy margins. The plant produces light purple flared campanulate flowers on numerous upright scapes well above the foliage beginning in late July and continuing for about five weeks.

2 Drawing Sheets

Latin name and variety denomination of the plant:
Botanical classification: *Hosta* hybrid (Tratt.).
Variety denomination: 'Wild Imagination'.

STATEMENT REGARDING PRIOR DISCLOSURES UNDER 37 CFR 1.77(B)(6)

The non-enabling disclosure of the claimed plant, in the form of cultivar registration with The American *Hosta* Society which is the International Cultivar Registration Authority for the genus *Hosta* was by the inventor in December 2020 with public printing in early 2021. No plants of *Hosta* 'Wild Imagination' have been sold, in this country or anywhere in the world, nor has any disclosure of the new plant been made, more than one year prior the filing date of this application, and such sale or disclosure within one year was either derived directly or indirectly from the inventor.

BACKGROUND AND ORIGIN OF THE PLANT

The present invention relates to a new and distinct *Hosta* plant, *Hosta* 'Wild Imagination' hereinafter also referred to as the new plant or just the cultivar name, 'Wild Imagination'. *Hosta* 'Wild Imagination' is the result of an intentional cross by the inventor on Jul. 31, 2012 at a wholesale perennial nursery greenhouse in Zeeland, Mich., USA. The female parent is *Hosta* 'Electrocution' (not patented) and the male parent is an unreleased proprietary hybrid known only by the breeder code H10-366 (not patented). The new plant passed initial evaluation in the summer of 2015, was give the breeder code 12-179-1 and was approved for final selection in the summer of 2018. The new plant has been asexually propagated by division at the same nursery in Zeeland, Mich., USA since 2016 and also by careful plant tissue culture with the resultant asexually propagated plants having retained all the same traits as the original plant. *Hosta* 'Wild Imagination' is stable and reproduces true to type in successive generations of asexual reproduction in both methods.

BRIEF SUMMARY OF THE PLANT

There are nearly 7,000 registered *Hosta* cultivars with The American *Hosta* Society, which is the International Cultivar Registration Authority for the genus *Hosta* along with a similar number of unregistered cultivars. The nearest comparison varieties are: 'Blue Cascade' (not patented), 'Curly Fries' (not patented), 'Silly String' U.S. Plant Pat. No. 32,127, 'Joy Ride' (not patented), 'Fulda' (not patented), and 'Neptune' U.S. Plant Pat. No. 19,674.

'Blue Cascade' has glaucous intensely wavy foliage, but the habit and leaves are smaller. 'Curly Fries' has a smaller habit, with more arching, narrower, chartreuse foliage that is less glaucous with less intense wavy margins. 'Silly String' has a smaller habit with narrower foliage and the flowers are darker purple. 'Joy Ride' has a smaller habit with broader and shorter leaf blades that have a coarser marginal wave. 'Fulda' has a smaller habit with more glaucous foliage that is flatter and more ovate, and the flowers are pale lavender on shorter scapes. 'Neptune' has a larger habit and larger and broader leaves that are more arching and the flowers, the scapes are more arching and flowers pale lavender.

'Electrocution' has narrower leaf blades that are less glaucous, more lustrous, more upright with a creamy white margin. The male parent had glaucous-blue, elongated wedge-shaped leaves and larger habit with a leaf margin that was not nearly as sinuate.

Other similar *Hostas* include: 'Elvis Lives' (not patented), 'Pineapple Poll' (not patented), and 'Blue Sliver' (not patented). 'Elvis Lives' (not patented) has a similar habit with shorter leaves, less sinuate margin and broader and less narrowly acute apices with a scape that is more erect with more numerous flowers. 'Pineapple Poll' has foliage with thinner-substance, narrower and leaf blades without glaucous surfaces with less intense sinuate margins. 'Blue Sliver' is a smaller plant with less undulation of the foliage and shorter and less narrowly acute apices.

*Hosta* 'Wild Imagination' is distinct from the *Hostas* listed above and all other cultivars known to the hybridizer by the following combined traits:

1. Medium-sized, rounded-mound plant habit with outwardly, glaucous, blue-green foliage;
2. Foliage has a long, narrowly-lanceolate apex that is moderately twisted with very wavy margins;
3. Light purple, flared, campanulate flowers, well above the foliage, on numerous scapes beginning in late July for about five weeks.

BRIEF DESCRIPTION OF THE DRAWINGS

The photographs of the new plant demonstrate the overall appearance of an eight-year-old plant, including the unique traits of 'Wild Imagination'. The colors are as accurate as reasonably possible with color reproductions. Ambient light spectrum, temperature, source and direction may cause the appearance of minor variation in color.

DETAILED BOTANICAL DESCRIPTION

Figure 1:
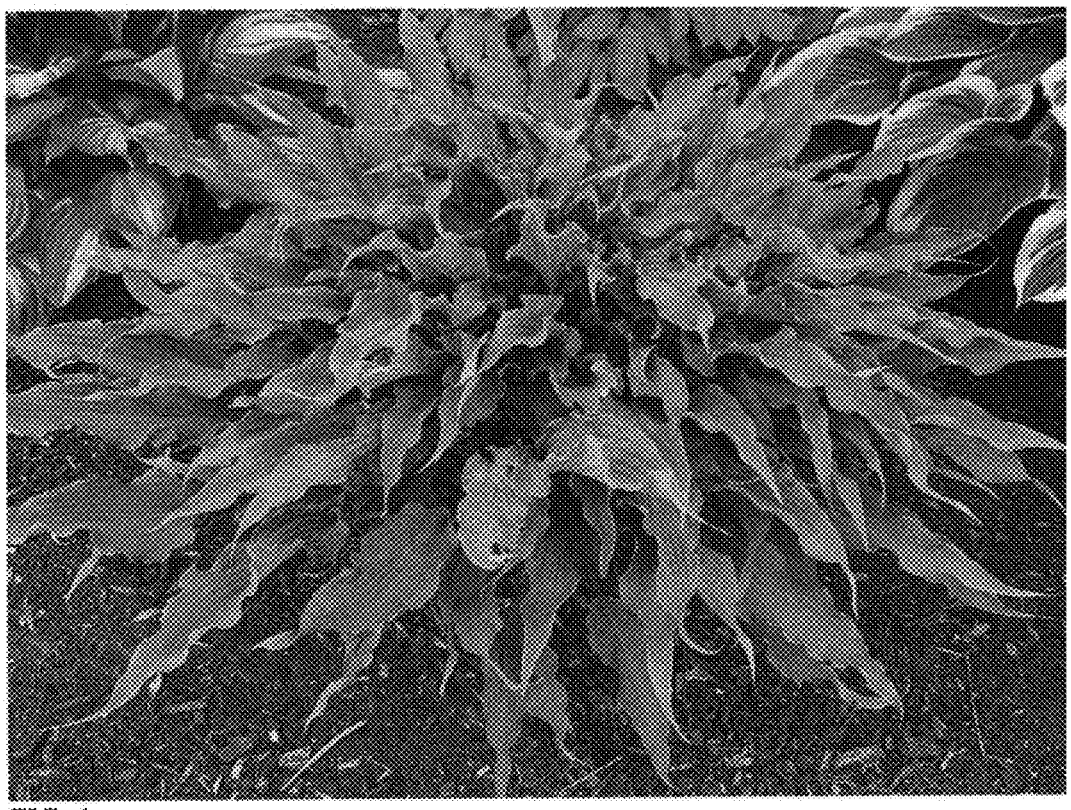
FIG. 1 shows a plant grown in a shaded trial garden with mid-summer foliage.
Figure 2:
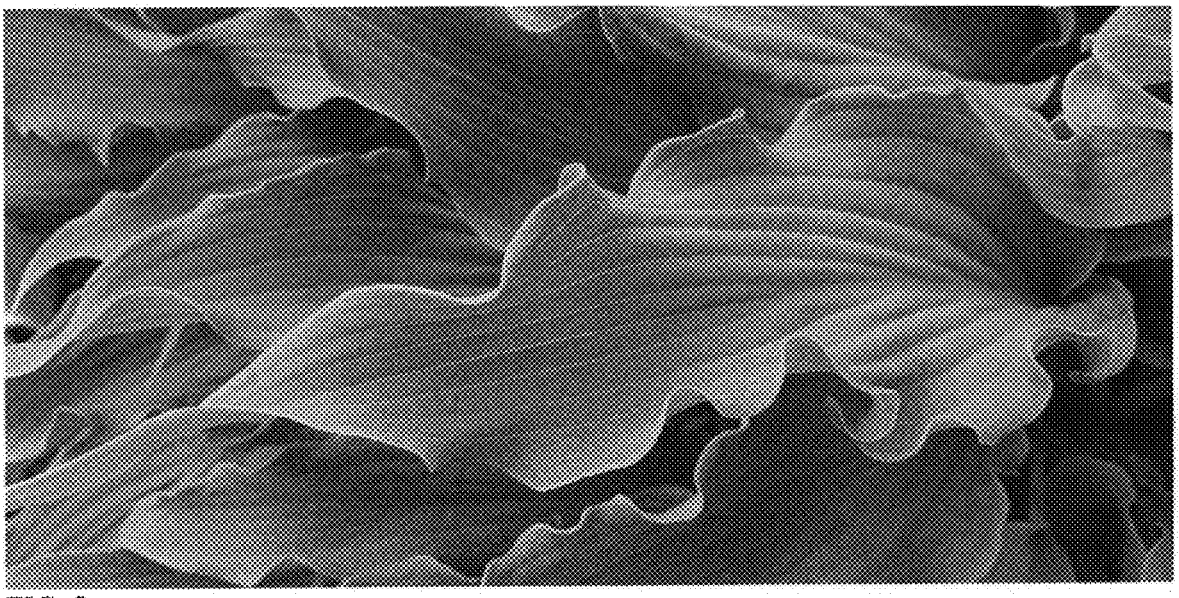
FIG. 2 shows a close-up of a twisted leaf with the wavy margins in early summer.
Figure 3:
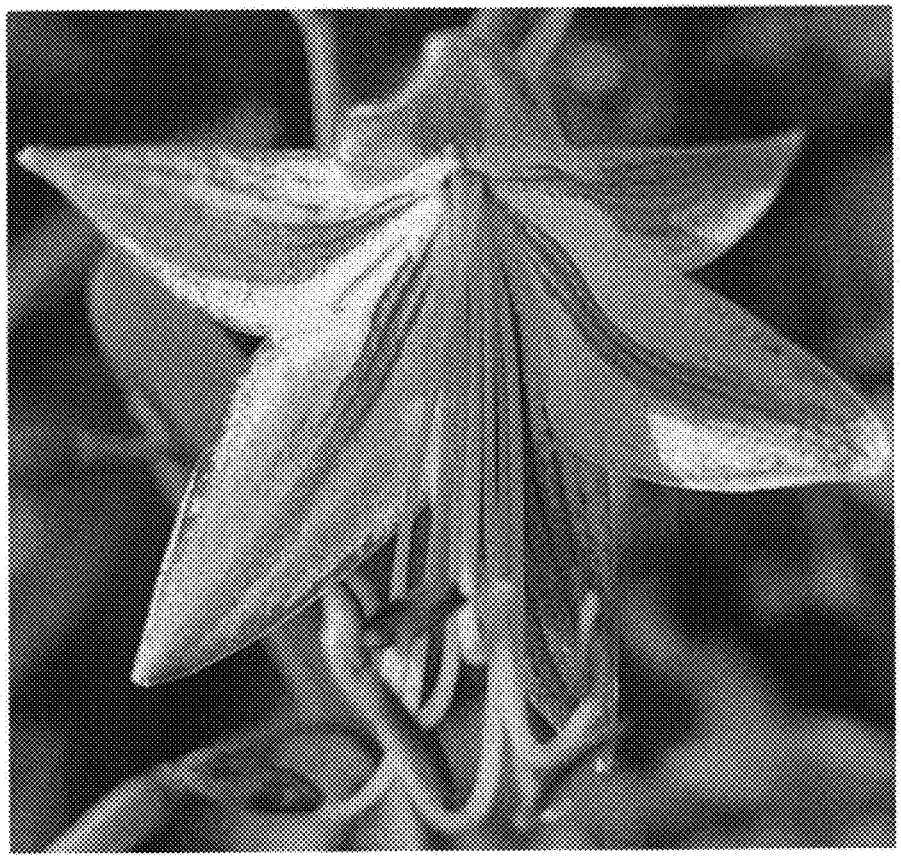
FIG. 3 shows a close-up of the inside of a flower.

The following descriptions and color references are based on the 2015 edition of The Royal Horticultural Society Colour Chart except where common dictionary terms are used. The new plant, *Hosta* 'Wild Imagination', has not been observed under all possible environments. The phenotype may vary slightly with different environmental conditions, such as temperature, light, fertility, moisture and maturity levels, but without any change in the genotype. The following observations and size descriptions are of an eight-year-old plant in a shaded trial garden in Zeeland, Mich. with supplemental water and fertilizer.

Botanical classification: *Hosta* hybrid;

Parentage: The female parent is 'Electrocution'; the male parent is known only by the breeder code H10-366 comprising 'Fulda' (not patented), 'Joy Ride' (not patented) and 'Neptune' (U.S. Plant Pat. No. 19,674);

Propagation: Garden division and sterile shoot-tip tissue culture;

Time to initiate roots from tissue culture: About two to three weeks;

Growth rate: Moderate;

Crop time: About 3 to 4 months to finish during the summer in a one-liter container from rooted tissue culture plantlet;

Rooting habit: Normal, fleshy, lightly branching;

Root color: Variable, nearest RHS 155D depending on soil type;

Plant shape and habit: Hardy herbaceous perennial with basal rosette of mostly outwardly pointed leaves emerging from rhizomes producing a large symmetrical rounded-mound of leaves;

Plant size: Foliage height to about 56 cm from the soil line to the top of the leaves and about 135 cm wide at the widest point slightly above the soil line;

Foliage description: Narrowly lanceolate; glabrous, moderately glaucous adaxial and abaxial; margin entire and heavily sinuate; narrowly acute and twisted apex with attenuate base; with slightly impressed veins;

Leaf blade size: To about 30.5 cm long and 9 cm wide;

Leaf blade color: Early season and shortly after emerging adaxial between RHS 137A and RHS 138A, abaxial between RHS N138C and RHS 137C; flowering season adaxial between RHS 122B and RHS 190B with wax and nearest RHS 137A with wax removed, abaxial nearest blend between RHS 189B and RHS N138C;

Petiole: Entire, glabrous, concavo-convex; mostly straight from base of plant to leaf base; to about 32 cm long and at base 10 mm across and 5 mm deep;

Petiole color: Adaxial distally nearest RHS 137C, proximally nearest RHS 147C becoming more maculate to nearly covering half the surface with nearest RHS N186C; abaxial distally between RHS 189B and RHS N138C, proximal seven-eighths nearest RHS 137C, distally nearest RHS 146C with maculate increasing distally to nearly 75% coverage with nearest RHS N186C; basal 1 cm of adaxial and abaxial between RHS NN155B and RHS NN155D with about 50% coverage of spots nearest RHS N186D;

Veins: Parallel; only lightly impressed adaxial, slightly costate abaxial; 6 to 8 pairs with one midrib, average 7 pairs;

Veins color: Adaxial proximally between RHS 122B and RHS 190 B, distally between RHS 146D and RHS 145A; abaxial between RHS 148D and RHS 145B, abaxial midrib nearest RHS 145D;

Flower description:

Buds one day prior to opening: Clavate with acute apex and narrow tubular base; about 52 mm long, apical bulb about 11 mm diameter and tube 10 mm long and about 3.5 mm diameter;

Bud color: Variable; distally between RHS 79D and RHS 83C, proximally nearest RHS 79D with an undertone of nearest RHS 148C, and a basal bulb region portions nearest RHS NN155D with stripes of nearest RHS 83C;

Flowers: Perfect; campanulate, funnelform with distally flaring tepals; actinomorphic; attitude outwardly to slightly drooping; about 40 mm wide and 69 mm long to exserted stigma, corolla portion 64 mm long and distally flared to 40 mm, fused tube portion about 22 mm long and 4 mm diameter (distal flowers smaller); persistent and drying on scape; effective for a normal period, typically one day on plant or as cut flower; scapes remain effective with flowers beginning early summer for about five weeks; about 34 flowers per scape; average spacing between flowers about 6 mm, significantly greater in proximal flowers;

Inflorescence: Flowering in upper 20 cm of peduncle and about 12 cm wide;

Flower period: Beginning late July and continuing for about five weeks to the end of August;

Floral bracts: Lanceolate; glaucous and glabrous both adaxial and abaxial; narrowly acute apex; truncate clasping base; enrolled proximally, flattened distally; upwardly extending about 45° from scape; to about 45 mm long and 11 mm wide near middle, decreasing distally; persisting after flowering;

Floral bract color: Adaxial nearest RHS 146C and abaxial nearest RHS 147C;

Cauline bracts: Typically one below initial flowers; lanceolate; narrowly acute apex; truncate clasping base; concavo-convex; to about 70 mm long and 13 mm wide; color same as floral bracts;

Flower fragrance: None detected;

Tepal: Six; two sets of three, glabrous, entire; both sets lanceolate to spatulate; with acute apex; fused in basal 42 mm;

*Inner set*.—About 65 mm long and about 11.0 mm wide.

*Inner set color*.—Not vitreous along margin; adaxial 4 mm wide margin nearest NN155D, center 3 veins nearest RHS 83B with surrounding center nearest RHS 83C, basal corolla tube portion nearest RHS NN155B with slight blush of nearest RHS 83C; abaxial between RHS 83C and RHS 83D with veins nearest RHS 83B.

*Outer set*.—About 65 mm long and 9 mm wide near fusion.

*Outer set color*.—Not vitreous along margin; 2 mm wide margin nearest NN155D, center 3 veins and distal 5 veins nearest RHS 83B with surrounding center and distal one-third nearest RHS 83C, basal corolla tube portion nearest RHS NN155B with slight blush of nearest RHS 83C; abaxial between RHS 83C and RHS 83D with veins nearest RHS 83B.

Gynoecium: Single; tri-carpelled; 69 mm long;

*Style*.—Single; cylindrical; approximately 65 mm long, 0.8 mm diameter, curved upward about 90° in distal 12 mm; color nearest RHS NN155B in distal one-third and transitioning to nearest RHS 145D in proximal one-third.

*Stigma*.—Globose, about 1 mm tall and 1 mm across; color nearest RHS NN155C.

*Ovary*.—Superior; ellipsoidal, lightly fluted longitudinally; about 4 mm long and 2.5 mm diameter at widest; acute apex and truncate base; color nearest RHS 145C.

Androecium: Six;

*Filaments*.—Cylindrical; approximately 65 mm long and 0.7 mm in diameter; curved around nearly 90° in the distal 12 mm; color nearest RHS NN155B distally and nearest RHS 145D proximally.

*Anthers*.—Elliptical; dorsifixed, longitudinally dehiscent; about 6.0 mm long and 2.5 mm wide and 1.5 mm thick; color between RHS 85C and RHS 85D with septal lines nearest RHS 79A prior to anthesis, post anthesis nearest RHS N77C.

*Pollen*.—Abundant; elliptic, less than 0.1 mm long; color nearest RHS 11B.

Peduncle: cylindrical; usually one per mature division and 56 per plant; glaucous and glabrous; upright; to about 92 cm tall, and up to about 5 mm in diameter at base; average about 87 cm tall and about 4.5 mm diameter at base;

Peduncle color: Distally nearest RHS 137B, proximally nearest RHS 137C heavily maculate with RHS N186C with spots overlapping to nearly solid RHS N186C;

Pedicel: Glabrous; glaucous; cylindrical; to 29 mm long and 1.5 mm diameter; attitude outwardly to slightly drooping;

Pedicel color: Proximally between RHS 148C and RHS 148B distally nearest RHS 83C;

Fruit: Tri-valved dehiscent capsule; oblong; apiculate apex and truncate base; lightly furrowed; about 15 mm long and 4 mm diameter; color as maturing nearest RHS 137A, at maturity between RHS 199A and RHS N199A;

Seed: Typically about 3 to 4 per capsule under natural cultivation; endospermic; flattened-elliptic wing surrounding embryo situated toward one end of ellipse; up to 6 mm long and 1.5 mm wide and 1 mm thick at embryo; color nearest RHS 202A;

Disease and pest tolerance and resistance: *Hosta* 'Wild Imagination' has not shown any resistance or susceptibility to pests and diseases except that common to *Hostas*.

Growth: The new plant grows best and shows best coloration with plenty of moisture, adequate drainage and light shade, but is able to tolerate some drought when mature.

Hardiness: At least from USDA zone 3 through 9.

It is claimed:

1. A new and distinct ornamental *Hosta* plant named 'Wild Imagination' as herein described and illustrated.

* * * * *